United States Patent
Ohno et al.

(10) Patent No.: US 12,333,728 B2
(45) Date of Patent: Jun. 17, 2025

(54) MEDICAL INFORMATION DISPLAY APPARATUS FOR DISPLAYING AN INDEX VALUE FOR THE LUNG, MEDICAL IMAGE PROCESSING APPARATUS FOR DERIVING THE INDEX VALUE, AND MEDICAL INFORMATION DISPLAY METHOD FOR DISPLAYING THE INDEX VALUE

(71) Applicants: FUJITA ACADEMY, Toyoake (JP); CANON MEDICAL SYSTEMS CORPORATION, Otawara (JP)

(72) Inventors: Yoshiharu Ohno, Toyoake (JP); Kota Aoyagi, Nasushiobara (JP)

(73) Assignees: FUJITA ACADEMY, Toyoake (JP); CANON MEDICAL SYSTEMS CORPORATION, Otawara (JP)

( * ) Notice: Subject to any disclaimer, the term of this patent is extended or adjusted under 35 U.S.C. 154(b) by 444 days.

(21) Appl. No.: 17/804,650

(22) Filed: May 31, 2022

(65) Prior Publication Data
US 2022/0383501 A1     Dec. 1, 2022

(30) Foreign Application Priority Data

May 31, 2021 (JP) ................. 2021-091184
May 30, 2022 (JP) ................. 2022-087650

(51) Int. Cl.
*G06T 7/00* (2017.01)
*A61B 6/00* (2024.01)
(Continued)

(52) U.S. Cl.
CPC ............ *G06T 7/0016* (2013.01); *A61B 6/032* (2013.01); *A61B 6/463* (2013.01); *G06T 7/11* (2017.01);
(Continued)

(58) Field of Classification Search
None
See application file for complete search history.

(56) References Cited

U.S. PATENT DOCUMENTS

2010/0074490 A1* 3/2010 Arakita ................. G06T 7/20
                                                                382/128
2014/0184608 A1   7/2014 Robb et al.
(Continued)

FOREIGN PATENT DOCUMENTS

JP    2019-10410 A       1/2019
WO    WO 2012/151579 A2  11/2012
WO    WO 2012/151579 A3  11/2012

OTHER PUBLICATIONS

Lung Texture Analysis, Imbio Report (2016) (1 page).
Extended European Search Report issued Nov. 2, 2022 in European Patent Application No. 22176501.9, 7 pages.

*Primary Examiner* — Thomas D Lee
(74) *Attorney, Agent, or Firm* — Oblon, McClelland, Maier & Neustadt, L.L.P.

(57) ABSTRACT

A medical information display apparatus according to an embodiment includes processing circuitry. The processing circuitry is configured to display information on the basis of volume data including at least a lung. The processing circuitry is configured to display a first index value based on an anatomical structure of the lung and a second index value based on the volume data related to the lung, so as to be kept in correspondence with each other.

11 Claims, 9 Drawing Sheets

(51) Int. Cl.
- *A61B 6/03* (2006.01)
- *A61B 6/46* (2024.01)
- *G06T 7/11* (2017.01)
- *G06T 7/187* (2017.01)
- *G06T 7/70* (2017.01)
- *G16H 30/40* (2018.01)
- *G16H 50/30* (2018.01)

(52) U.S. Cl.
CPC ............... *G06T 7/187* (2017.01); *G06T 7/70* (2017.01); *G16H 30/40* (2018.01); *G16H 50/30* (2018.01); *G06T 2207/10081* (2013.01); *G06T 2207/20021* (2013.01); *G06T 2207/30061* (2013.01); *G06T 2207/30096* (2013.01)

(56) References Cited

U.S. PATENT DOCUMENTS

| | | |
|---|---|---|
| 2015/0269325 A1 | 9/2015 | Ohta et al. |
| 2015/0327780 A1* | 11/2015 | Kano .................. A61B 90/37 600/407 |
| 2016/0310094 A1 | 10/2016 | Kobayashi et al. |
| 2018/0061049 A1 | 3/2018 | Robb et al. |
| 2019/0005644 A1 | 1/2019 | Yaguchi et al. |
| 2021/0049766 A1 | 2/2021 | Kondo et al. |
| 2021/0104044 A1 | 4/2021 | Yaguchi et al. |

* cited by examiner

MEDICAL INFORMATION DISPLAY APPARATUS FOR DISPLAYING AN INDEX VALUE FOR THE LUNG, MEDICAL IMAGE PROCESSING APPARATUS FOR DERIVING THE INDEX VALUE, AND MEDICAL INFORMATION DISPLAY METHOD FOR DISPLAYING THE INDEX VALUE

CROSS-REFERENCE TO RELATED APPLICATIONS

This application is based upon and claims the benefit of priority from Japanese Patent Application No. 2021-091184, filed on May 31, 2021; the entire contents of which are incorporated herein by reference.

FIELD

Embodiments described herein relate generally to a medical information display apparatus, medical image processing apparatus, medical information display method, and a computer program product.

BACKGROUND

Conventionally, a method is known by which, for diffuse lung diseases for example, a distribution of lesions is quantified for subregions of the lungs, so as to display a lesion amount of each lung region in a polar map. Accordingly, there is a demand for techniques capable of visualizing a quantitative distribution of lesions in an organ or a tissue, for the reason that diagnosing processes can be made easier, for example.

In some situations, diseases may occur or develop along an anatomical structure of an organ or a tissue. In examples of lung diseases such as diffuse lung diseases, a lesion may spread along the extent of a bronchus, or pathological conditions may vary between a distal part and a proximal part of a bronchus. In other words, in diagnoses and treatment of lesions, it is important to understand the relationship between a three-dimensional distribution of the lesions and the anatomical structure of the organ or the tissue.

DETAILED DESCRIPTION

Figure 1:
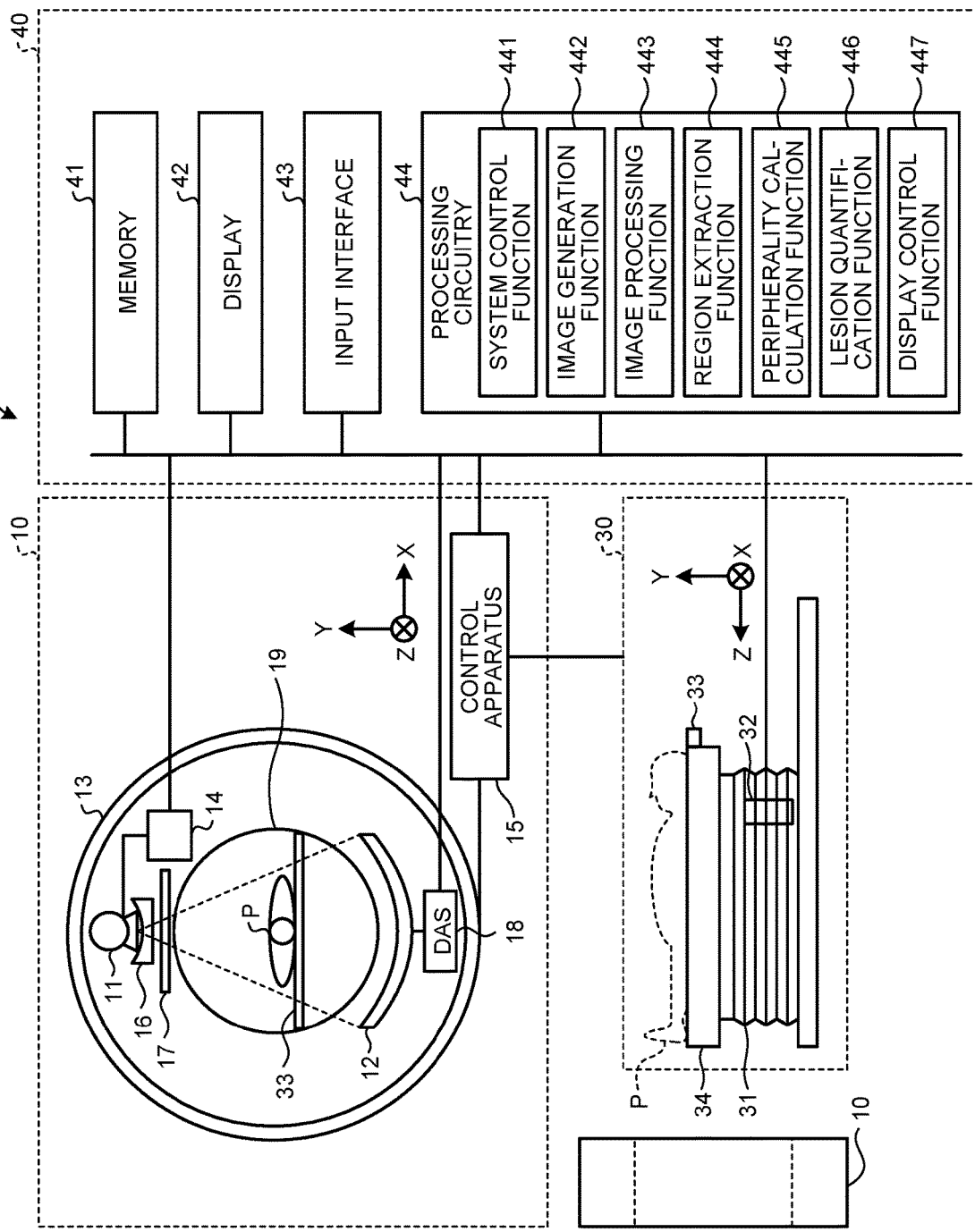
FIG. 1 is a diagram illustrating an exemplary configuration of an X-ray Computed Tomography (CT) apparatus in which a medical information display apparatus or a medical image processing apparatus according to an embodiment is installed.

A medical information display apparatus according to an embodiment includes processing circuitry. The processing circuitry is configured to display information on the basis of volume data including at least a lung. The processing circuitry is configured to display a first index value based on an anatomical structure of the lung and a second index value based on the volume data related to the lung, so as to be kept in correspondence with each other.

The following describes a medical information display apparatus, a medical image processing apparatus, a medical information display method, a medical image processing method, and a computer program product according to embodiments with reference to the accompanying drawings. In the following description, components having the same or substantially the same function as those described above with respect to the previously described drawings will be denoted by the same symbols, and a duplicate description will be given only when necessary. Even when the same part is represented, the dimensions or proportions thereof may be represented in different ways depending on the drawings. From the viewpoint of ensuring the visibility of the drawings, for example, only major or representative components in the description of each of the drawings may be denoted by reference symbols, and even components having the same or substantially the same function are not necessarily denoted by reference symbols.

The embodiments described below exemplify cases in which the medical information display apparatus or the medical image processing apparatus according to one or more of the embodiments is installed in the X-ray CT apparatus.

The medical information display apparatuses and the medical image processing apparatuses according to the embodiments are not limited to the case in which the apparatuses are each installed in the X-ray CT apparatus and may be implemented as an independent apparatus by a computer having a processor and memories such as a read only memory (ROM) and a random access memory (RAM) as hardware resources. In this case, the processor installed in the computer can implement various kinds of functions according to the embodiments by executing a computer program read from the ROM or the like and loaded onto the RAM.

The medical information display apparatuses and the medical image processing apparatuses according to the embodiments may each be implemented by being installed in another medical image diagnostic apparatus different from the X-ray CT apparatus. In this case, the processor installed in each medical image diagnostic apparatus can implement the functions according to the embodiments by executing a computer program read from the ROM or the like and loaded onto the RAM. Various kinds of functions according to the embodiments can be implemented. Examples of the other medical image diagnostic apparatus include various medical image diagnostic apparatuses such as X-ray diagnostic apparatuses, magnetic resonance imaging (MRI) apparatuses, ultrasonic diagnostic apparatuses, single photon emission computed tomography (SPECT) apparatuses, positron emission computed tomography (PET) apparatuses, SPECT-CT apparatuses, in which a SPECT apparatus and an X-ray CT apparatus are integrated with each other, and PET-CT apparatuses, in which a PET apparatus and an X-ray CT apparatus are integrated with each other.

X-ray CT apparatuses include various types such as the third-generation CT and the fourth-generation CT, for example; any of these types can be used for the embodiments. The third-generation CT is of the rotate/rotate type, in which an X-ray tube and a detector integrally rotate around a subject. The fourth-generation CT is the stationary/rotate type, in which many X-ray detection elements arranged in a ring shape are fixed, with only the X-ray tube rotating around the subject.

First Embodiment

FIG. 1 is a diagram of an example of the configuration of an X-ray CT apparatus 1 in which a medical information display apparatus or a medical image processing apparatus according to an embodiment is installed. The X-ray CT apparatus 1 applies X-rays from an X-ray tube 11 to a subject P and detects the applied X-rays with an X-ray detector 12. The X-ray CT apparatus 1 generates a CT image about the subject P based on output from the X-ray detector 12.

As illustrated in FIG. 1, the X-ray CT apparatus 1 has a frame 10, a couch 30, and a console 40. For the convenience of description, FIG. 1 depicts a plurality of frames 10. The frame 10 is a scanning apparatus having a configuration to take an X-ray CT image of the subject P. The couch 30 is a conveyance apparatus for placing the subject P to be subjected to X-ray CT imaging and positioning the subject P. The console 40 is a computer controlling the frame 10. The frame 10 and the couch 30 are installed in a CT examination room, whereas the console 40 is installed in a control room adjacent to the CT examination room, for example. The frame 10, the couch 30, and the console 40 are mutually communicably connected to each other in a wired or wireless manner.

The console 40 is not necessarily required to be installed in the control room. The console 40 may be installed in the same room together with the frame 10 and the couch 30, for example. The console 40 may be incorporated into the frame 10.

In the present embodiment, a rotating shaft of a rotating frame 13 in a non-tilted state or the longitudinal direction of a couchtop 33 of a couch 30 is defined as a Z-axial direction, an axial direction orthogonal to the Z-axial direction and horizontal to a floor surface is defined as an X-axial direction, and an axial direction orthogonal to the Z-axial direction and perpendicular to the floor surface is defined as a Y-axial direction.

As illustrated in FIG. 1, the frame 10 has the X-ray tube 11, the X-ray detector 12, the rotating frame 13, an X-ray high voltage apparatus 14, a control apparatus 15, a wedge 16, a collimator 17, and a data acquisition system (DAS) 18.

The X-ray tube 11 is a vacuum tube having a cathode (filament) generating thermoelectrons and an anode (target) generating X-rays upon collision with the thermoelectrons. The X-ray tube 11 applies the thermoelectrons from the cathode toward the anode using high voltage supplied from the X-ray high voltage apparatus 14 to apply X-rays to the subject P.

The hardware generating X-rays is not limited to the X-ray tube 11. In place of the X-ray tube 11, a fifth-generation system may be used to generate X-rays, for example. The fifth-generation system includes a focus coil focusing an electron beam generated from an electron gun, a deflection coil electromagnetically deflecting the electron beam, and a target ring surrounding half the subject P to generate X-rays upon collision with the deflected electron beam.

The X-ray detector 12 detects the X-rays emitted from the X-ray tube 11 and having passed through the subject P and outputs an electric signal corresponding to a detected X-ray dose to the DAS 18. The X-ray detector 12 has a row of X-ray detection elements in which a plurality of X-ray detection elements are arranged in a channel direction along one arc centered on the focal point of the X-ray tube 11, for example. The X-ray detector 12 has a structure in which a plurality of X-ray detection elements are arranged in a slice direction (a row direction) in the channel direction, for example. The X-ray detector 12 is an indirect conversion type detector having a grid, a scintillator array, and an optical sensor array, for example. The scintillator array has a plurality of scintillators. The scintillator has a scintillator crystal outputting light with a light amount corresponding to an incident X-ray dose. The grid is placed on a face of the scintillator array on its X-ray incident plane side and has an X-ray blocking plate having the function of absorbing scattered X-rays. The grid may also be referred to as a collimator (a one-dimensional collimator or a two-dimensional collimator). The optical sensor array has the function of converting the light from the scintillators into an electric signal corresponding to the light amount of the light. A photomultiplier tube (PMT) is used as the optical sensor, for example. The X-ray detector 12 may be a direct conversion type detector having a semiconductor element converting incident X-rays into an electric signal.

The rotating frame 13 is an annular frame supporting the X-ray tube 11 and the X-ray detector 12 such that they face each other and rotates the X-ray tube 11 and the X-ray detector 12 by the control apparatus 15 described below. An image field of view (FOV) is set in an aperture 19 of the rotating frame 13. The rotating frame 13 is a casting made of aluminum, for example. In addition to the X-ray tube 11 and the X-ray detector 12, the rotating frame 13 can further support the X-ray high voltage apparatus 14, the wedge 16, the collimator 17, and the DAS 18. The rotating frame 13 can also further support various components not illustrated in FIG. 1.

The X-ray high voltage apparatus 14 has a high voltage generation apparatus and an X-ray control apparatus. The high voltage generation apparatus has an electric circuit such as a transformer and a rectifier and generates high voltage to be applied to the X-ray tube 11 and a filament current to be supplied to the X-ray tube 11. The X-ray control apparatus controls output voltage according to the X-rays emitted by the X-ray tube 11. The high voltage generation apparatus may be of the transformer system or of the inverter system. The X-ray high voltage apparatus 14 may be provided in the rotating frame 13 in the frame 10 or be provided in a fixed frame (not illustrated) in the frame 10. The fixed frame is a frame rotatably supporting the rotating frame 13.

The control apparatus 15 includes drive mechanisms such as motors and actuators and processing circuitry having a processor and a memory to control the drive mechanisms. The control apparatus 15 receives input signals from an input interface 43, an input interface provided in the frame 10, or the like to perform operation control of the frame 10 and the couch 30. Examples of the operation control by the control apparatus 15 include control to rotate the rotating frame 13, control to tilt the frame 10, and control to operate the couch 30. The control to tilt the frame 10 is implemented by the control apparatus 15 rotating the rotating frame 13 about an axis parallel to the X-axial direction according to inclination angle (tilt angle) information input through the input interface mounted on the frame 10. The control apparatus 15 may be provided in the frame 10 or be provided in the console 40.

The wedge 16 is a filter for regulating an X-ray dose emitted from the X-ray tube 11. Specifically, the wedge 16 is a filter passing and attenuating the X-rays applied from the X-ray tube 11 so that the X-rays applied from the X-ray tube 11 to the subject P have distribution set in advance. The wedge 16 is a wedge filter or a bow-tie filter and is formed by machining aluminum or the like so as to have a certain target angle and a certain thickness, for example.

The collimator 17 limits the application range of the X-rays having passed through the wedge 16. The collimator 17 supports a plurality of lead plates blocking X-rays in a slidable manner and adjusts the form of a slit formed by the lead plates. The collimator 17 may also be called an X-ray aperture.

The DAS 18 reads the electric signal corresponding to the X-ray dose detected by the X-ray detector 12 from the X-ray detector 12. The DAS 18 amplifies the read electric signal and integrates (adds) the electric signal over a view period to collect detection data having digital values corresponding to an X-ray dose over the view period. The detection data is called projection data. The DAS 18 is implemented by an application specific integrated circuit (ASIC) in which a circuit element that can generate the projection data is installed, for example. The projection data is transmitted to the console 40 via a non-contact data transmission apparatus or the like.

The detection data generated by the DAS 18 is transmitted to a receiver having a photodiode provided in a non-rotating part of the frame 10 (e.g., the fixed frame, which is not illustrated in FIG. 1) through optical communication from a transmitter having a light emitting diode (LED) provided in the rotating frame 13 and is transferred to the console 40. The method for transmitting the detection data from the rotating frame 13, which is a rotating part, to the non-rotating part of the frame 10 is not limited to the optical communication described above; any method may be adopted so long as it is non-contact data transfer.

The present embodiment describes the X-ray CT apparatus 1 in which the X-ray detector 12 of an integral type is installed as an example; the technology according to the present embodiment can also be implemented as the X-ray CT apparatus 1 in which a photon counting type X-ray detector is installed.

The couch 30 is an apparatus placing and moving the subject P to be scanned. The couch 30 has a base 31, a couch drive apparatus 32, the couchtop 33, and a support frame 34. The base 31 is a casing supporting the support frame 34 in a vertically movable manner. The couch drive apparatus 32 is a drive mechanism moving the couchtop 33 on which the subject P is placed in the longitudinal direction of the couchtop 33. The couch drive apparatus 32 includes motors and actuators. The couchtop 33 is a board on which the subject P is placed. The couchtop 33 is provided on a top face of the support frame 34. The couchtop 33 can protrude from the couch 30 toward the frame 10 so that the whole body of the subject P can be imaged. The couchtop 33 is formed of carbon fiber reinforced plastic (CFRP), for example, which has good X-ray permeability and physical properties such as rigidity and strength. The inside of the couchtop 33 is hollow, for example. The support frame 34 supports the couchtop 33 in a movable manner in the longitudinal direction of the couchtop 33. In addition to the couchtop 33, the couch drive apparatus 32 may move the support frame 34 in the longitudinal direction of the couchtop 33.

The console 40 has a memory 41, a display 42, the input interface 43 and processing circuitry 44. Data communication among the memory 41, the display 42, the input interface 43, and the processing circuitry 44 is performed via a bus. Although the console 40 is described as a separate unit from the frame 10, the frame 10 may include the console 40 or part of the components of the console 40.

The memory 41 is implemented by a semiconductor memory element such as a ROM, a RAM, or a flash memory, a hard disk, or an optical disc, for example. The memory 41 stores therein the projection data and reconstructed image data, for example. The memory 41 stores therein various kinds of computer programs, for example. The memory 41 stores therein a model 100 described below, for example. The storage area of the memory 41 may be located within the X-ray CT apparatus 1 or be within an external storage apparatus connected with a network. The memory 41 is an example of a storage unit.

The display 42 displays various types of information. The display 42 displays medical images (CT images) generated by the processing circuitry 44 and a graphical user interface (GUI) for receiving various kinds of operations from an operator, for example. The information displayed on the display 42 includes a spatial distribution of lesions with respect to an anatomical structure according to the embodiment. As the display 42, any various displays can be used as appropriate. As the display 42, a liquid crystal display (LCD), a cathode ray tube (CRT) display, an organic electro luminescence display (OELD), or a plasma display can be used, for example.

The display 42 may be provided anywhere in the control room. The display 42 may be provided in the frame 10. The display 42 may be of a desktop type or include a tablet terminal or the like that can wirelessly communicate with the console 40 main body. One or two or more projectors may be used as the display 42. The display 42 is an example of a display unit.

The input interface 43 receives various kinds of input operations from the operator, converts the received input operations into electric signals, and outputs them to the processing circuitry 44. The input interface 43 receives collection conditions when collecting the projection data, reconstruction conditions when reconstructing the CT image, and image processing conditions when generating a post-processed image from the CT image from the operator, for example. Further, for example, the input interface 43 receives, from the operator, a calculation condition or the like used at the time of calculating a distribution of lesion amounts with respect to an anatomical structure on the basis of CT image data.

As the input interface 43, a mouse, a keyboard, a trackball, a switch, a button, a joystick, a touchpad, or a touch panel display can be used as appropriate, for example. In the present embodiment, the input interface 43 is not limited to those including these physical operating components. Examples of the input interface 43 include electric signal processing circuitry receiving an electric signal corresponding to an input operation from an external input device provided separately from the apparatus and outputting this electric signal to the processing circuitry 44. The input interface 43 may be provided in the frame 10. The input interface 43 may include a tablet terminal or the like that can wirelessly communicate with the console 40 main body. The input interface 43 is an example of an input unit.

The processing circuitry 44 controls the operation of the entire X-ray CT apparatus 1. The processing circuitry 44 has a processor and memories such as a ROM and a RAM as hardware resources. The processing circuitry 44 executes a system control function 441, an image generation function 442, an image processing function 443, a region extraction function 444, a peripherality calculation function 445, a lesion quantification function 446, a display control function 447 and the like by the processor executing a computer program loaded onto the memory. The processing circuitry 44 is an example of a processing unit.

In the system control function 441, the processing circuitry 44 controls various kinds of functions of the processing circuitry 44 based on input operations received from the operator via the input interface 43. The processing circuitry 44 controls CT scan performed by the frame 10, for example. The processing circuitry 44 acquires volume data related to the subject P by implementing the image generation function 442 and the image processing function 443 (explained later) on the basis of the detection data acquired in the CT scan. In the present embodiment, an example will be explained in which the volume data including at least the lungs is acquired.

In this situation, the processing circuitry 44 may acquire the volume data related to the subject P from the outside of the X-ray CT apparatus 1. Further, although the present embodiment is explained with an example using the volume data acquired by the X-ray CT apparatus 1, for instance, it is also acceptable to use volume data acquired by another medical image diagnostic apparatus. In the present example, the processing circuitry 44 implementing the image generation function 442 is an example of the acquisition unit.

In the image generation function 442, the processing circuitry 44 generates data in which pre-processing such as logarithmic conversion processing, offset correction processing, inter-channel sensitivity correction processing, or beam hardening correction is performed on the detection data output from the DAS 18. The processing circuitry 44 stores the generated data in the memory 41. The data before the pre-processing (the detection data) and the data after the pre-processing may collectively be referred to as the projection data. The processing circuitry 44 performs reconstruction processing using the filtered back projection method, the successive approximation reconstruction method, machine learning, or the like on the generated projection data (the projection data after the pre-processing) to generate CT image data. The processing circuitry 44 stores the generated CT image data in the memory 41.

In the image processing function 443, the processing circuitry 44 converts the CT image data generated by the image generation function 442 into tomographic image data of a given section or three-dimensional image data by a known method based on input operations received from the operator via the input interface 43. The processing circuitry 44 applies three-dimensional image processing such as volume rendering, surface rendering, image value projection processing, multi-planar reconstruction (MPR) processing, or curved MPR (CPR) processing to the CT image data to generate rendered image data in a given viewpoint direction, for example. The generation of the three-dimensional image data, that is, volume data such as the rendered image data in a given viewpoint direction may be performed directly by the image generation function 442. The processing circuitry 44 stores the tomographic image data or the three-dimensional image data in the memory 41.

In the region extraction function 444, the processing circuitry 44 extracts the bronchi included in the volume data. The processing circuitry 44 performs a segmentation on the bronchi on the basis of the volume data. In this situation, the segmentation performed on the bronchi denotes separating a bronchi region from the surrounding tissue of the bronchi, i.e., a lung parenchyma region. The segmentation on the bronchi may be performed by using a publicly-known method. As for the bronchi region, when it is possible to extract the bronchi region by performing a segmentation on the region other than the bronchi such as the lung parenchyma, it is also acceptable to extract the bronchi region by performing the segmentation on the region other than the bronchi. Further, the processing circuitry 44 identifies branch parts of the bronchi on the basis of a result of the segmentation. The processing circuitry 44 identifies the section positioned on the head side of the first branch part as the trachea and identifies the section positioned on the peripheral side of the first branch part as the bronchi. For example, the processing circuitry 44 may identify the side where the other branch parts are present as the peripheral side. In this situation, the processing circuitry 44 implementing the region extraction function 444 is an example of the region extraction unit. Further, the extent of the extracted bronchi is an example of an anatomical structure of the lungs.

For example, in the region extraction function 444, the processing circuitry 44 performs the segmentation on the bronchi by using a region growing method. In this situation, among data points of the volume data, for example, the processing circuitry 44 sets a data point satisfying a predetermined CT value condition as a starting point. The predetermined CT value condition may be, for example, a CT value being equal to a CT value of air or having a magnitude approximate to the CT value of air. From among data points in the vicinity of the starting point being set, the processing circuitry 44 adds certain data points satisfying the CT value condition to the region. After that, the processing circuitry 44 performs the segmentation to obtain the region to be extracted as the bronchi region, by expanding the region until there is no more data point satisfying the CT value condition in the vicinity of the data points included in the region.

For example, in the region extraction function 444, the processing circuitry 44 is also capable of performing the segmentation on the bronchi while using a machine learning model. In this situation, the machine learning model is a parameterized composite function in which a plurality of mathematical functions are combined, so as to receive an input of volume data and to output volume data within the volume data that indicates the bronchi region. The parameterized composite function is defined by a combination of a plurality of adjustable mathematical functions and parameters. The machine learning model may be any parameterized composite function satisfying the abovementioned requirements, but may be assumed as a multilayer network model. In one example, the machine learning model may be a Deep Neural Network (DNN). The DNN may be a DNN having any structure, and it is possible to use, for example, a Residual Network (ResNet), a Dense Convolutional Network (DenseNet), or a U-Net. The configuration and the parameters of the machine learning model may be determined in advance and stored in the memory 41, for example.

In the peripherality calculation function 445, the processing circuitry 44 calculates a degree of peripherality (hereinafter, "peripherality degree") at each of the evaluation points in the lung parenchyma, on the basis of the extracted bronchi region. In this situation, the evaluation points in the lung parenchyma are assumed to be arbitrary values belonging to the lung parenchyma region among various values of volume data. Further, the peripherality degree is assumed to be an index indicating, with respect to an arbitrary evaluation point, how peripheral the evaluation point is positioned in the lungs along the extent of the bronchi. In this situation, the processing circuitry 44 implementing the peripherality calculation function 445 is an example of the calculation unit. Further, the evaluation points in the lung parenchyma serve as examples of arbitrary evaluation points in the volume data. Also, the peripherality degree is an example of the first index value.

Figure 2:
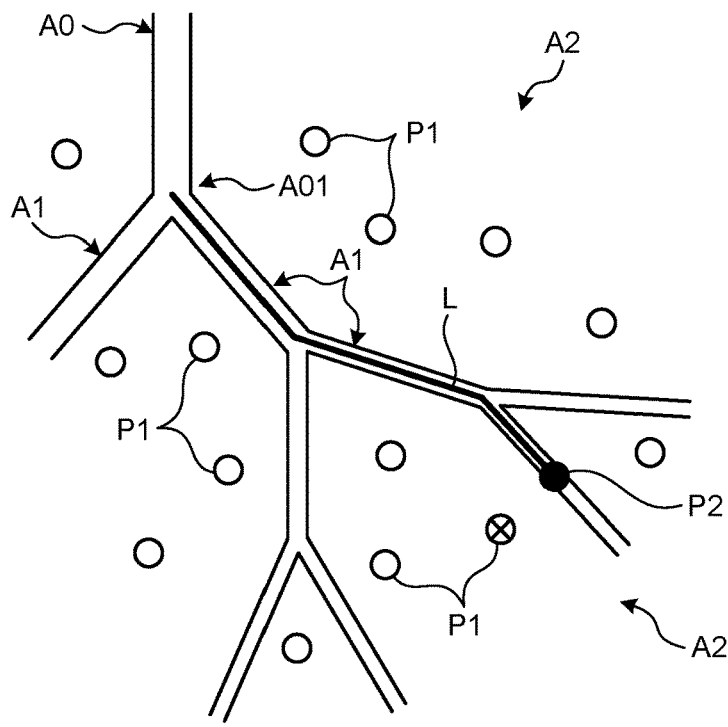
FIG. 2 is a drawing for explaining an example of a peripherality calculation process according to the embodiment.

Next, the calculation of the peripherality degree will be explained, with reference to the drawings. FIG. 2 is a drawing for explaining an example of the peripherality calculation process according to the embodiment. FIG. 2 schematically illustrates a trachea region A0, a bronchi region A1, and a lung parenchyma region A2. Further, FIG. 2 schematically illustrates a plurality of evaluation points P1. In the present example, among the plurality of evaluation points P1, a peripherality calculation process will be explained with regard to an arbitrary evaluation point P1 indicated with a circled X in FIG. 2.

In the peripherality calculation function 445, the processing circuitry 44 specifies a data point P2 that is in the bronchi region A1 and is positioned nearest to the evaluation point P1. As the peripherality degree, the processing circuitry 44 calculates a distance L from a trachea branch part A01 on the central side to the data point P2 on the peripheral side, within the extracted bronchi region A1. In this situation, it is assumed that the trachea branch part A01 is a connection part between the trachea region A0 and the bronchi region A1. As described herein, the peripherality degree according to the embodiment is information defining a position in the lung parenchyma region A2 on the basis of the extent of the bronchi and is a continuous value that becomes larger as more branch parts are passed, i.e., as the position becomes more peripheral.

The peripherality degree does not necessarily have to be the distance L itself and may be expressed with a value that varies in accordance with the distance L, such as a value obtained by normalizing the distance L by the length of the trachea region A0 or the maximum length of the bronchi region A1, for example. In another example, the peripherality degree may be set so as to be smaller as the position becomes more peripheral, such as a reciprocal of the distance from the trachea branch part A01 described above, for example.

Further, instead of the distance from the trachea branch part A01, the processing circuitry 44 may calculate a distance including the trachea region A0 as a peripherality degree.

In the present example, as the nearest data point P2, the processing circuitry 44 may use a single data point or may use two or more data points. When using two or more data points, for example, the nearest data point P2 and the second nearest data point may be used.

When there are two or more nearest data points P2 with respect to one evaluation point P1, the processing circuitry 44 may calculate the peripherality degree according to a predetermined rule. In one example, the processing circuitry 44 may adopt the highest peripherality degree among the two or more nearest data points. In another example, the processing circuitry 44 may adopt the lowest peripherality degree among the two or more nearest data points. In yet another example, the processing circuitry 44 may adopt an average value of the peripherality degrees of the two or more nearest data points. It is assumed that these rules are determined in advance and stored in the memory 41 or the like.

In the lesion quantification function 446, the processing circuitry 44 derives an index value related to a lesion amount of the lungs, on the basis of the volume data. The lesions may be certain elements of which a spatial distribution is difficult to understand such as, for example, inflammation, fibrosis, alveolar hemorrhage, pulmonary edema, tumor, or the like. In the present embodiment, the index value related to the lesions is explained as an example; however, it is also acceptable to use an index value related to another property or characteristic of the lesions such as a state quantity correlated with the lesions. In the present example, the index value related to the lesion amount of the lungs is an index value based on volume data related to the lungs, from volume data including at least a lung. For example, the index value related to the lesion amount of the lungs is lesion information of the lungs indicating the presence/absence or a level of a lesion of an arbitrary type at each of the evaluation points in the lung parenchyma. In one example, the index value may be an arbitrary voxel value or pixel value belonging to the lung parenchyma region, from the volume data or image data based on the volume data. Further, as the index value, a value based on the voxel value or the pixel value may be used. As for the value based on the voxel value or the pixel value, it is acceptable to use a value indicating whether or not the voxel value or the pixel value satisfies a predetermined threshold value range or a statistical value such as a value resulting from normalization or a standard deviation value. The voxel value or the pixel value may express a CT value. For example, when CT values are used, each of the CT values may be compared with a predetermined threshold value. For example, when a CT value satisfies a threshold value condition, the voxel or the pixel can be treated as an evaluation point at which the presence of a lesion is derived. In the following description, the index value related to the lesion amount of the lungs may simply be referred to as lesion information.

The techniques related to the present embodiment are also applicable to index values related to lesions of any type. Further, to derive the index value related to the lesion amount according to the present embodiment, it is acceptable to use any extraction method for extracting the lesions or a state quantity correlated with the lesions. In one example, the processing circuitry 44 may classify the lung parenchyma into a plurality of texture patterns on the basis of the volume data, similarly to the technique disclosed in Japanese Patent Application Laid-open No. 2019-010410. The plurality of texture patterns are each a texture pattern in a CT image and include a texture pattern characteristic to an arbitrary lesion. For instance, examples of a texture pattern characteristic to lesions of a diffuse lung disease include a ground-glass opacity.

Further, in the lesion quantification function 446, the processing circuitry 44 generates distribution information about the lesion amounts with respect to an anatomical structure, on the basis of the derived lesion information at the evaluation points and the peripherality degrees at the evaluation points calculated by the peripherality calculation function 445. In this situation, the distribution information about the lesion amounts with respect to the anatomical structure denotes information indicating a relationship between the peripherality degrees and the lesion amounts. In the present example, the processing circuitry 44 implementing the lesion quantification function 446 is an example of the derivation unit. Further, the index value related to the lesion amount is an example of the second index value.

In an example, the lesion amount may be the quantity of evaluation points at which the presence of the lesion has been derived. When the evaluation points are uniformly distributed spatially, the quantity of evaluation points is correlated with the volume of the lesions in the lung parenchyma. In another example, the lesion amount may be a percentage of the quantity of evaluation points at which the presence of the lesion has been derived, among the evaluation points belonging to each peripherality degree or each section of peripherality degrees. When the evaluation points are uniformly distributed spatially, the percentage of the evaluation points indicates the volume of the lesions occupying regions of the lung parenchyma corresponding to different peripherality degrees. When the evaluation points are not uniformly distributed spatially, it is desirable to normalize the quantity of the evaluation points at which the presence of the lesion has been derived, by using the quantity of evaluation points per unit volume or the like. With this arrangement, while understanding the distribution of the lesions with respect to the anatomical structure with a focus placed on a partial site of the lungs, it is also possible to keep calculation costs low by reducing the quantity of evaluation points in the other sites of the lungs.

In the display control function 447, the processing circuitry 44 displays images on the display 42 based on the various kinds of image data generated by the image processing function 443. The images to be displayed on the display 42 include an image indicating the distribution information about the lesion amounts with respect to the anatomical structure that was derived by the lesion quantification function 446. In other words, the processing circuitry 44 causes the display 42 to display the peripherality degrees and the lesion information so as to be kept in correspondence with each other. The images to be displayed on the display 42 include a CT image based on the CT image data, a sectional image based on the sectional image data of a given section, and a rendered image in a given viewpoint direction based on the rendered image data in a given viewpoint direction. The images to be displayed on the display 42 include an image for displaying an operation screen and an image for displaying notifications and warnings to the operator. The processing circuitry 44 implementing the display control function 447 is an example of a display controller.

In this situation, image data indicating the distribution information about the lesion amounts with respect to the anatomical structure may be generated by any function selected from among: the image processing function 443, the lesion quantification function 446, and the display control function 447.

Each of the functions 441 to 447 is not limited to being implemented by a single piece of processing circuitry. Each of the functions 441 to 447 may be implemented by combining a plurality of independent processors with each other to form the processing circuitry 44 and causing each of the processors to execute each computer program. Each of the functions 441 to 447 may be implemented distributed or integrated as appropriate in a single piece or a plurality of pieces of processing circuitry.

Although the console 40 has been described as a single console executing a plurality of functions, separate consoles may execute the functions. The functions of processing circuitry 44 such as the image generation function 442, the image processing function 443, the region extraction function 444, the peripherality calculation function 445, the lesion quantification function 446, and the like may be distributed, for example.

Part or the whole of the processing circuitry 44 is not limited to being included in the console 40 and may be included in an integrated server collectively performing processing on the detection data acquired by a plurality of medical image diagnostic apparatuses.

At least one piece of processing out of post-processing, region extraction processing, peripherality calculation processing, lesion quantification processing, and display processes may be performed by either the console 40 or an external workstation. The processing may be processed by both the console 40 and the workstation at the same time. As the workstation, a computer having a processor implementing functions corresponding to the respective pieces of processing and memories such as a ROM and a RAM as hardware resources can be used as appropriate, for example.

In the reconstruction of the X-ray CT image data, either reconstruction system of a full-scan reconstruction system and a half-scan reconstruction system may be applied. In the image generation function 442, the processing circuitry 44 uses the projection data for the surroundings of the subject P, or 360 degrees in the full-scan reconstruction system, for example. In the half-scan reconstruction system, the processing circuitry 44 uses the projection data for 180 degrees+a fan angle. In the following, for the sake of the simplicity of description, it is assumed that the processing circuitry 44 uses the full-scan reconstruction system performing reconstruction using the projection data for the surroundings of the subject P, or 360 degrees.

The technology according to the present embodiment can also be applied to both single-tube X-ray computed tomography apparatuses and what is called multi-tube X-ray computed tomography apparatuses in which a plurality of pairs of an X-ray tube and a detector are installed in a rotating ring.

The technology according to the present embodiment can also be applied to the X-ray CT apparatus 1 configured to enable imaging by a dual-energy system. In this case, the X-ray high voltage apparatus 14 can alternately switch the energy spectrum of the X-rays emitted from the X-ray tube 11 by fast switching between two kinds of voltage values, for example. That is to say, the X-ray CT apparatus 1 is configured to be capable of collecting the projection data in each collection view while modulating a tube voltage at timing following a control signal for tube voltage modulation. By imaging a subject at different tube voltages, light and shade contrast in the CT image can be improved based on the energy permeability of a material for each X-ray energy spectrum.

It is assumed that the X-ray CT apparatus 1 according to the present embodiment is configured to read an electric signal from the X-ray detector 12 by a sequential reading system.

The X-ray CT apparatus 1 according to the present embodiment may be configured as an upright CT. In this case, a patient support mechanism configured to be capable of supporting the subject P in an upright position and moving it along a rotating shaft of the rotating part of the frame 10 may be provided in place of the movement of the couchtop 33. The X-ray CT apparatus 1 according to the present embodiment may be configured as a mobile CT in which the frame 10 and the couch 30 are movable.

Figure 3:
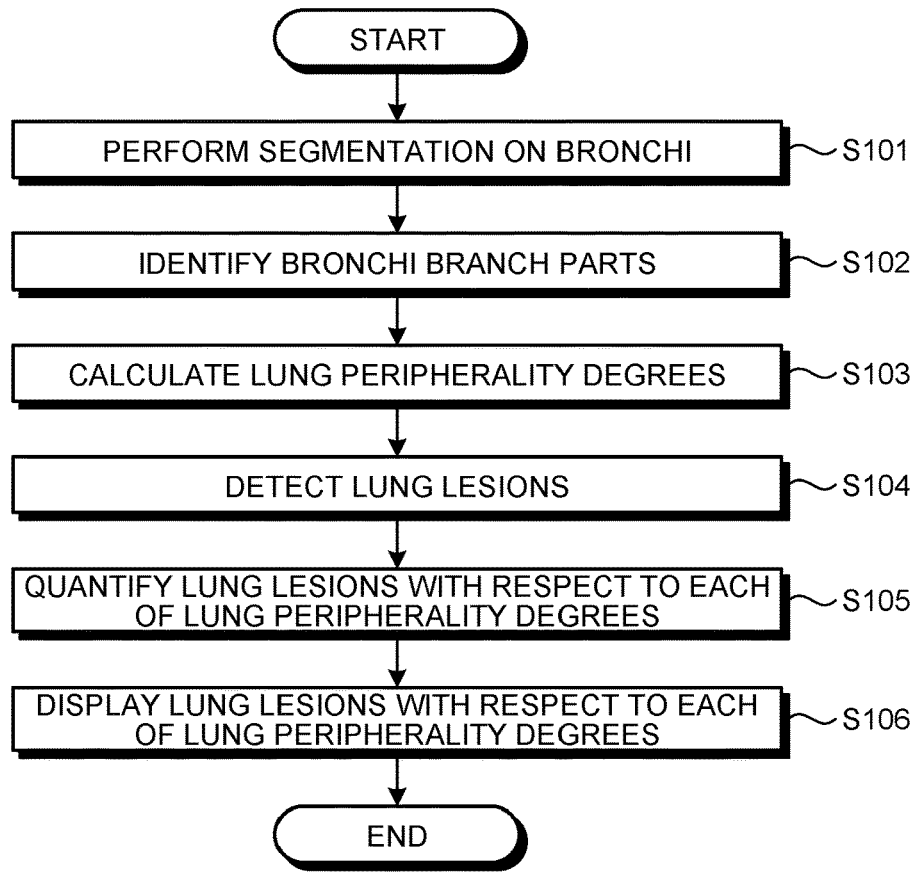
FIG. 3 is a flowchart illustrating an example of a process of displaying a distribution of lesion amounts with respect to an anatomical structure according to the embodiment.

FIG. 3 is a flowchart illustrating an example of the process of displaying the distribution of the lesion amounts with respect to an anatomical structure according to the embodiment. It is assumed that the workflow described below is carried out after the system control function 441 acquires the volume data including at least a lung.

At first, the region extraction function 444 performs the segmentation on the bronchi on the basis of the volume data (step S101). Further, on the basis of a result of the segmentation, the region extraction function 444 identifies branch parts of the bronchi (step S102). After that, on the basis of the extracted bronchi region, the peripherality calculation function 445 calculates a peripherality degree at each of the evaluation points in the lung parenchyma (step S103).

By detecting lung lesions on the basis of the volume data, the lesion quantification function 446 derives an index value related to lesion amounts of the lungs (step S104). The process at the present step may be performed prior to the process at step S101 or may be performed in parallel to the processes at steps S101 through S103.

Further, on the basis of the lung peripherality degrees and the lung lesion information, the lesion quantification function 446 quantifies the lung lesions with respect to each of the lung peripherality degrees (step S105). In other words, the lesion quantification function 446 generates distribution information about the lesion amounts with respect to the anatomical structure. Further, the display control function 447 causes the display 42 to display the generated distribution information about the lesion amounts with respect to the anatomical structure (step S106). After that, the workflow in FIG. 3 ends.

Figure 4:
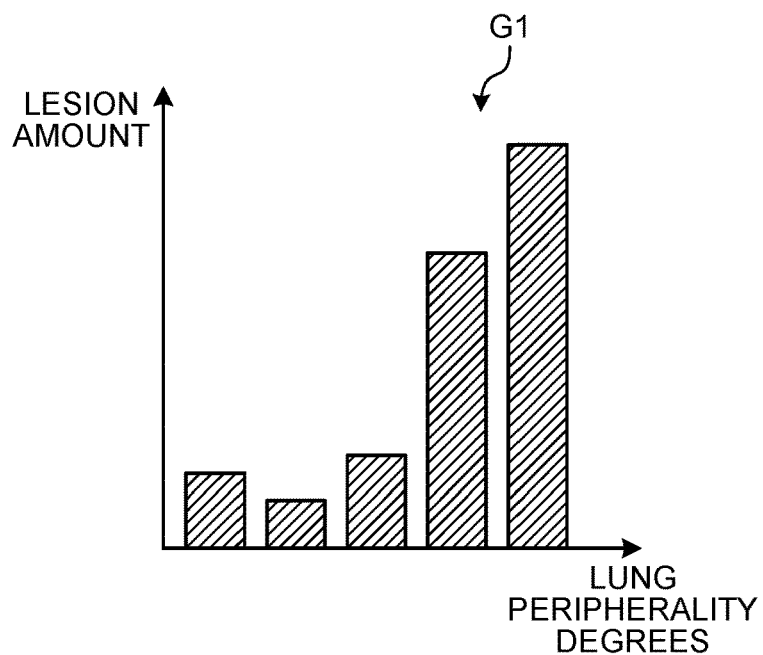
FIG. 4 is a graph illustrating an example of displaying the distribution of lesion amounts with respect to the anatomical structure according to the embodiment.

Next, the display of the distribution information about the lesion amounts with respect to the anatomical structure will be explained, with reference to the drawings. FIG. 4 is a graph illustrating an example of the display of the distribution of the lesion amounts with respect to the anatomical structure according to the embodiment. In the graph in FIG. 4, the vertical axis and the horizontal axis express lesion amounts and lung peripherality degrees, respectively. In one example, the processing circuitry 44 generates image data for displaying a graph that indicates magnitude of the lesion amounts with respect to the peripherality degrees, as the distribution information about the lesion amounts with respect to the anatomical structure. On the basis of the generated image data, the display control function 447 causes the display 42 to display an image G1 including the graph that indicates the magnitude of the lesion amounts with respect to the lung peripherality degrees. According to an aspect in which the graph illustrated in FIG. 4 is displayed, it is possible to understand how the lesions are three-dimensionally distributed along the extent of the bronchi.

As explained above, in the X-ray CT apparatus 1 in which the medical image processing apparatus according to the embodiment is installed, the processing circuitry 44 is configured to be capable of implementing the system control function 441, the region extraction function 444, the peripherality calculation function 445, and the lesion quantification function 446. In the system control function 441, the processing circuitry 44 acquires the volume data including at least a lung. In the region extraction function 444, the processing circuitry 44 extracts the bronchi included in the volume data. In the peripherality calculation function 445, the processing circuitry 44 calculates the lung peripherality degrees at the arbitrary evaluation points in the volume data, on the basis of the extracted bronchi. In the lesion quantification function 446, the processing circuitry 44 derives the index value related to the lesion amounts of the lungs, on the basis of the volume data.

With the configurations described above, it is possible to assign the lung peripherality degrees to the evaluation points in the lung parenchyma along the extent of the bronchi. Further, on the basis of the lung peripherality degrees, it is possible to divide the lung region into subregions and to quantify the lesions in each of the divided subregions. In this situation, the extent of the bronchi is an example of the anatomical structure of the lungs. In other words, by using the medical image processing apparatus according to the embodiment, it is possible to evaluate the distribution of the lesion amounts with respect to the anatomical structure.

Further, in the X-ray CT apparatus 1 in which the medical image processing apparatus according to the embodiment is installed, the processing circuitry 44 is configured to be capable of further implementing the display control function 447. Further, in the X-ray CT apparatus 1 in which the medical information display apparatus according to the embodiment is installed, the processing circuitry 44 is configured to be capable of implementing the display control function 447. In the display control function 447, the processing circuitry 44 presents the display based on the volume data including at least a lung. In one example, the processing circuitry 44 displays the peripherality degrees based on the extent of the bronchi included in the lungs and the lesion amounts of the lungs so as to be kept in correspondence with each other. For example, the processing circuitry 44 causes the display 42 to display the display information in which the peripherality degrees and the lesion amounts are kept in correspondence with each other.

With the configurations described above, it is possible to display the correspondence between the lung peripherality degrees assigned to the evaluation points in the lung parenchyma along the extent of the bronchi and the lesion amounts in the divided subregions obtained by dividing the lung region on the basis of the lung peripherality degrees. By using the display mode described herein, the spatial distribution of the lesions is made easier to understand. In other words, by using the medical information display apparatus according to the embodiment, it is possible to provide information that is useful for diagnosing various types of diseases and the like. In this situation, the extent of the bronchi is an example of the anatomical structure of the lungs. In other words, by using the medical information display apparatus according to the embodiment, it is possible to evaluate the distribution of the lesion amounts with respect to the anatomical structure.

For example, with the novel coronavirus pneumonia, it is known that bilateral ground-glass opacity often appear in the lung periphery. In relation to this, the medical information display apparatus according to the embodiment is capable of displaying the information quantified along the lung peripherality degrees with regard to the ground-glass opacity appearing as lesions. Consequently, an operator of the medical information display apparatus according to the embodiment is able to easily judge whether or not an acquired CT image is an image characteristic to the novel coronavirus pneumonia.

Second Embodiment

Figure 5:
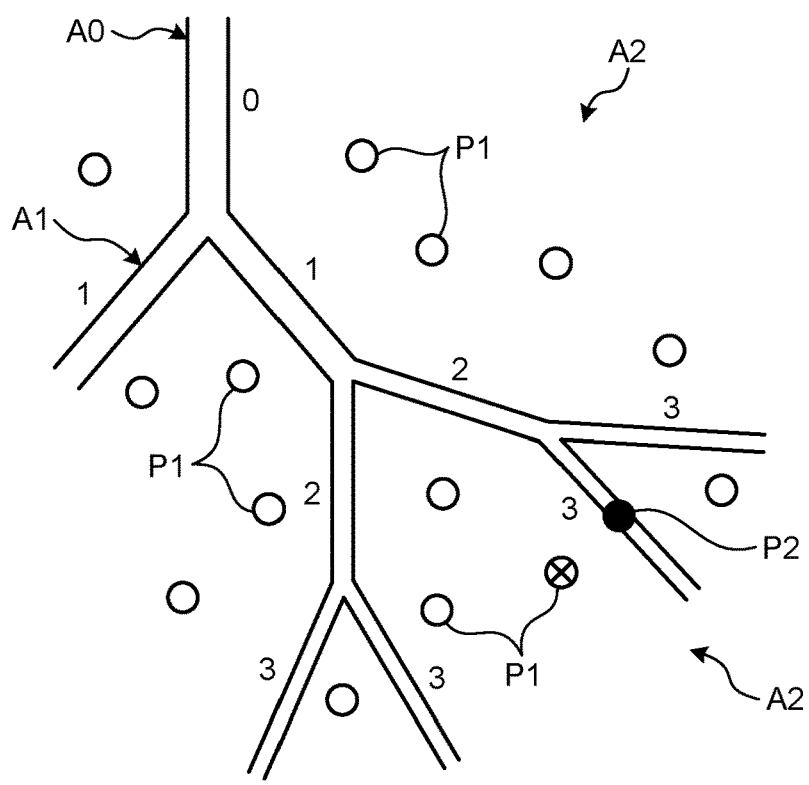
FIG. 5 is a drawing for explaining another example of the peripherality calculation process according to the embodiment.

In a second embodiment, differences from the first embodiment will primarily be explained. FIG. 5 is a drawing for explaining another example of the peripherality calculation process according to the embodiment. FIG. 5 schematically illustrates the trachea region A0, the bronchi region A1, and the lung parenchyma region A2. Further, FIG. 5 schematically illustrates the plurality of evaluation points P1. In the present example, among the plurality of evaluation points P1, a peripherality calculation process will be explained with regard to the arbitrary evaluation point P1 indicated with a circled X in FIG. 5.

In the region extraction function 444, while setting the trachea region A0 with ordinal number 0, the processing circuitry 44 sets the quantity of branches, i.e., the quantity of branch parts, that are passed while advancement is made from the trachea region A0 through the bronchi region A1 toward the peripheral side, as the ordinal number of each of the regions within the bronchi region A1. For example, the processing circuitry 44 sets the ordinal number of the bronchi region A1 connected to the trachea region A0 via the trachea branch part A01 to 1. As another example, the processing circuitry 44 sets the ordinal number of another bronchi region A1 to 2, which is connected via a branch part to the peripheral side of the bronchi region A1 of which the ordinal number is 1.

In the peripherality calculation function 445, the processing circuitry 44 specifies the data point P2 that is in the bronchi region A1 and is positioned nearest to the evaluation point P1. The processing circuitry 44 calculates the ordinal number of the bronchi region A1 in which the data point P2 is positioned as a peripherality degree.

As explained above, the peripherality degrees according to the present embodiment are each a discrete value that becomes larger as more branch parts are passed, i.e., as the position becomes more peripheral. With this configuration also, it is possible to achieve advantageous effects similar to those of the embodiment described above.

Third Embodiment

Figure 6:
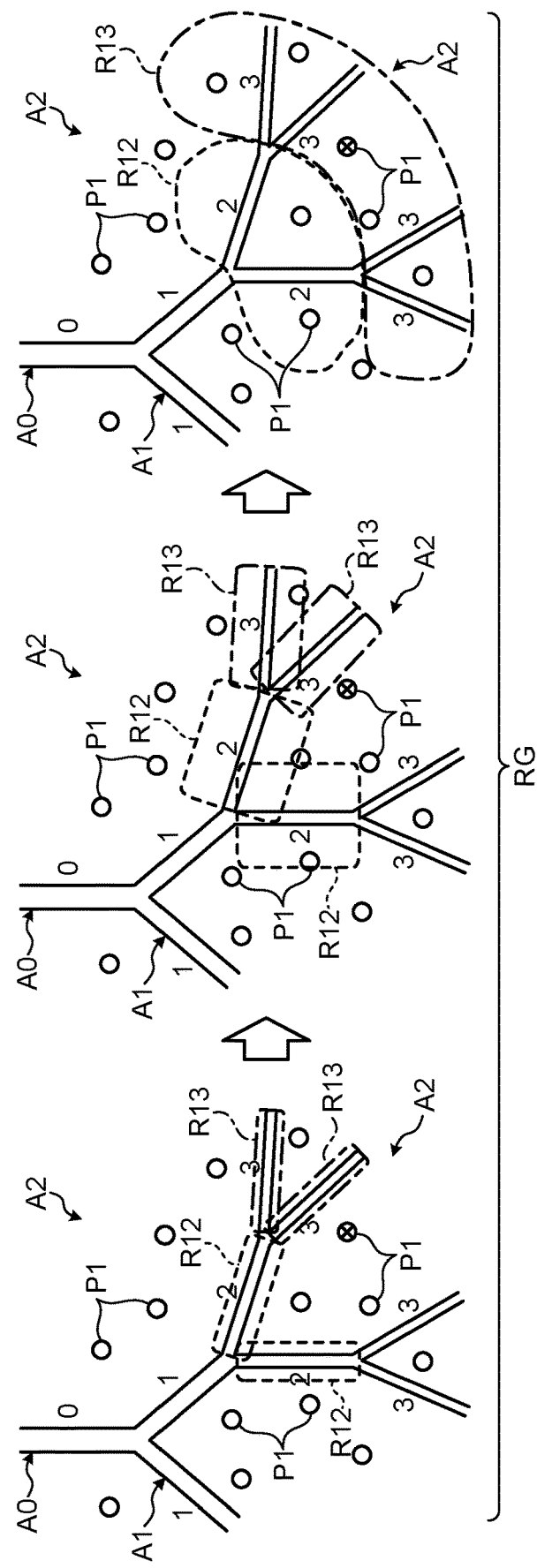
FIG. 6 is a drawing for explaining yet another example of the peripherality calculation process according to the embodiment.

In a third embodiment, differences from the second embodiment will primarily be explained. FIG. 6 is a drawing for explaining yet another example of the peripherality calculation process according to the embodiment. As illustrated in FIG. 6, similarly to the segmentation performed on the bronchi by the region extraction function 444, the peripherality calculation function 445 according to the present embodiment expands a plurality of bronchi regions A1 having mutually the same ordinal number, by using a region growing method within the lung parenchyma region A2.

In a region growing process RG implementing the region growing method in FIG. 6, when the evaluation points P1 in the lung parenchyma region A2 satisfy a predetermined condition, the evaluation points P1 are added to coupled regions R12 and R13 to be sequentially expanded. The coupled region R12 in FIG. 6 is a region formed as a result of expanding a plurality of bronchi regions A1 of each of which the ordinal number is 2 by using the region growing method and further coupling the expanded regions onto a plurality of lung parenchyma regions A2. Similarly, the coupled region R13 in FIG. 6 is a region formed in the lung parenchyma regions A2 as a result of expansion from a plurality of bronchi regions A1 of each of which the ordinal number is 3.

In the peripherality calculation function 445, the processing circuitry 44 calculates the ordinal number of the bronchi region A1 serving as a starting point for forming the coupled regions, as a peripherality degree of each of the evaluation points P1 in the coupled regions. In the example in FIG. 6, with respect to each of all the evaluation points P1 in the coupled region R12 formed from the plurality of bronchi regions A1 of each of which the ordinal number is 2, the peripherality degree is calculated as 2.

As explained above, the peripherality degrees according to the present embodiment have constant magnitude within each of the coupled regions R12 and R13 and are expressed with the ordinal number of the bronchi region A1 serving as the starting point of the region growing (expansion) process. With this configuration also, it is possible to achieve advantageous effects similar to those of the embodiments described above.

Fourth Embodiment

In a fourth embodiment, differences from the first embodiment will primarily be explained. In the embodiments described above, the example was explained in which the peripherality degrees are calculated so as to become larger as advancement is made toward the peripheral side along the extent of the bronchi; however, possible embodiments are not limited to this example.

Figure 7:
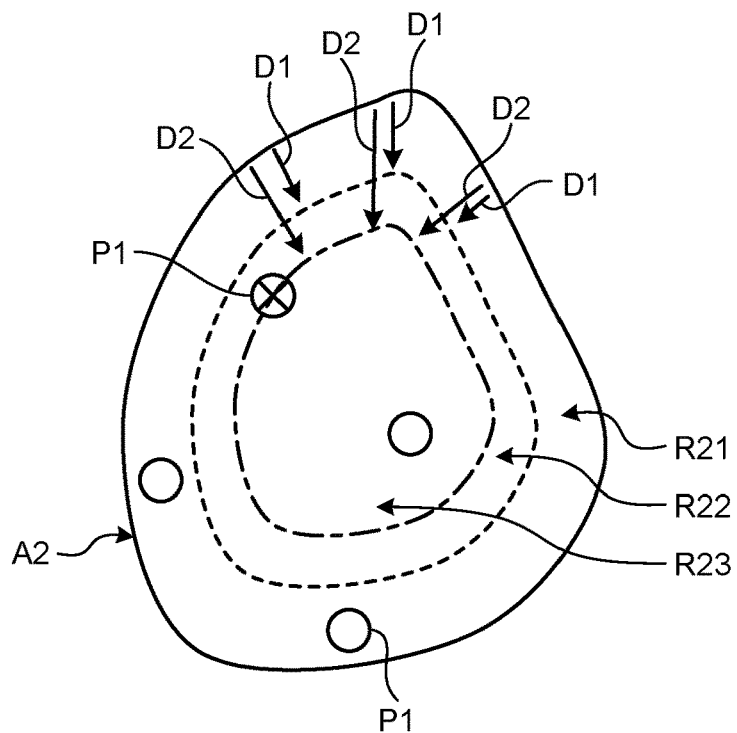
FIG. 7 is a drawing for explaining yet another example of the peripherality calculation process according to the embodiment.

FIG. 7 is a drawing for explaining yet another example of the peripherality calculation process according to the embodiment. FIG. 7 illustrates an arbitrary region among regions of a lung. In the present embodiment, the regions of the lung denote regions of lung lobes, lung segments, or the like obtained by dividing the lungs into a plurality of anatomical regions. In the present example, the outer shapes of the regions of the lung serve as an example of the anatomical structure of the lung. The outer shapes of the regions are defined by boundary planes between the regions. Further, the inside of the boundaries of the regions includes, at least, a bronchi region A1 and a lung parenchyma region A2. Further, FIG. 7 schematically illustrates a plurality of evaluation points P1. In the present example, among the plurality of evaluation points P1, a peripherality calculation process will be explained with regard to an arbitrary evaluation point P1 indicated with a circled X in FIG. 7.

In an example, in the peripherality calculation function 445, with respect to the evaluation point P1, the processing circuitry 44 calculates a continuous value corresponding to a depth D2 from the boundary plane between the regions to the inside of the boundary, as a peripherality degree of the evaluation point P1.

Alternatively, in the peripherality calculation function 445, with respect to the evaluation point P1, the processing circuitry 44 may calculate a discrete value indicating an ordinal number of a section corresponding to the depth from the boundary plane between the regions to the inside of the boundary, as a peripherality degree of the evaluation point P1. For example, the processing circuitry 44 sets the ordinal number of a region R21 from the boundary plane between the regions to a depth D1 to 1. For example, the processing circuitry 44 sets the ordinal number of a region R22 from the depth D1 to the depth D2 of the regions to 2. For example, the processing circuitry 44 sets the ordinal number of a region R23 positioned on the peripheral side of the depth D2 of the regions, i.e., positioned on the inside of the regions, to 3.

As explained above, the peripherality degrees according to the present embodiment are calculated in accordance with the depths from the boundary plane between the regions to the inside of the boundary, with respect to the regions of the lung. With this configuration also, it is possible to achieve advantageous effects similar to those of the embodiments described above.

Alternatively, it is also acceptable to calculate peripherality degrees in accordance with depths from the outer surface of the entire lungs to the inside thereof.

Further, the peripherality degrees according to the above embodiments may also be used in combination. For example, it is also possible to calculate a sum or an average value of the peripherality degrees according to any of the embodiments, as a peripherality degree of each of the evaluation points P1. In that situation, it is also possible to apply weights that are different among a plurality of peripherality degrees. For example, to the peripherality degrees according to the first embodiment, the second embodiment, or the third embodiment, it is possible to apply a weight larger than a weight applied to the peripherality degrees according to the fourth embodiment.

Fifth Embodiment

Figure 8:
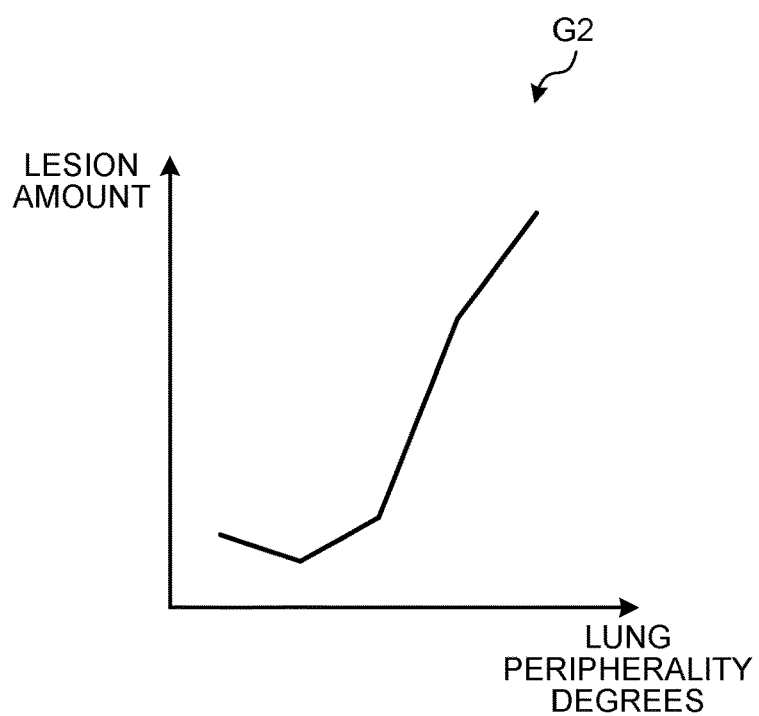
FIG. 8 is a graph illustrating another example of displaying a distribution of lesion amounts with respect to the anatomical structure according to the embodiment.

In a fifth embodiment, differences from the first embodiment will primarily be explained. The display of the distribution information about the lesion amounts with respect to the anatomical structure is not limited to using the image G1 explained with reference to FIG. 4. FIG. 8 is a graph illustrating another example of the display of a distribution of the lesion amounts with respect to the anatomical structure according to the embodiment. As illustrated in FIG. 8, the display control function 447 may cause the display 42 to display an image G2 including a graph indicating magnitude of lesion amounts with respect to the lung peripherality degrees. In other words, the display mode of the graph indicating the magnitude of the lesion amounts with respect to the lung peripherality degrees may be a bar graph as illustrated in FIG. 2 or may be a line graph as illustrated in FIG. 8. By using this display mode also, it is possible to achieve advantageous effects similar to those of the first embodiment.

Sixth Embodiment

Figure 9:
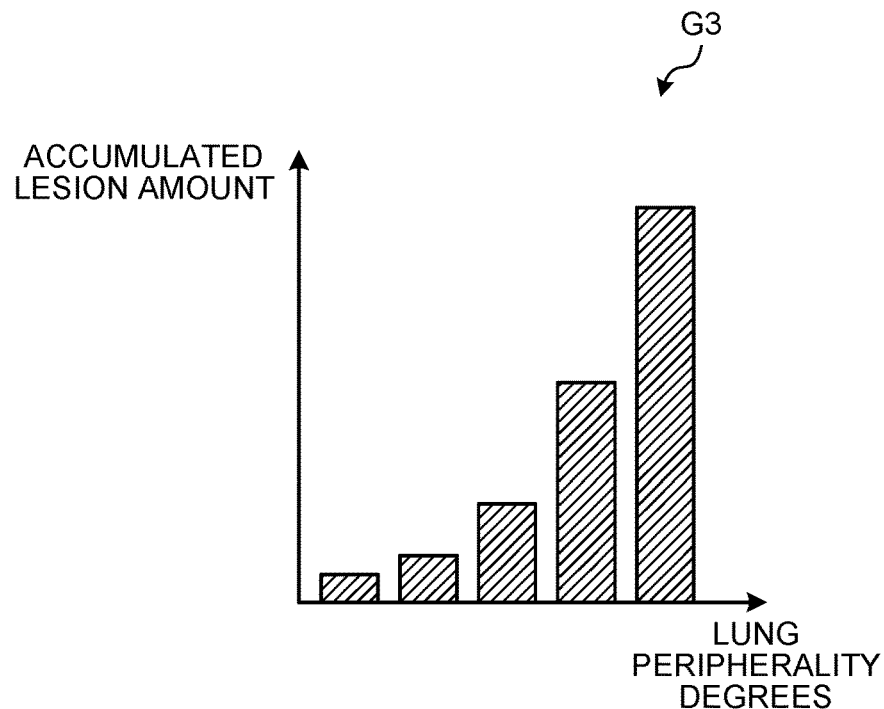
FIG. 9 is a graph illustrating yet another example of displaying a distribution of lesion amounts with respect to the anatomical structure according to the embodiment.

In a sixth embodiment, differences from the first embodiment will primarily be explained. FIG. 9 is a graph illustrating yet another example of the display of a distribution of lesion amounts with respect to the anatomical structure according to the embodiment. As illustrated in FIG. 9, the display of distribution information about the lesion amounts with respect to the anatomical structure may be realized by displaying an image G3 including a graph indicating accumulate values of the lesion amounts with respect to the lung peripherality degrees, i.e., magnitude of accumulated lesion amounts. The graph in the image G3 illustrated in FIG. 9 is a bar graph similarly to the graph in FIG. 4. By using this display mode also, it is possible to achieve advantageous effects similar to those of the first embodiment. Further, from the accumulated lesion amounts, it is also possible to quantitatively understand total amounts of the lesion amounts.

Seventh Embodiment

Figure 10:
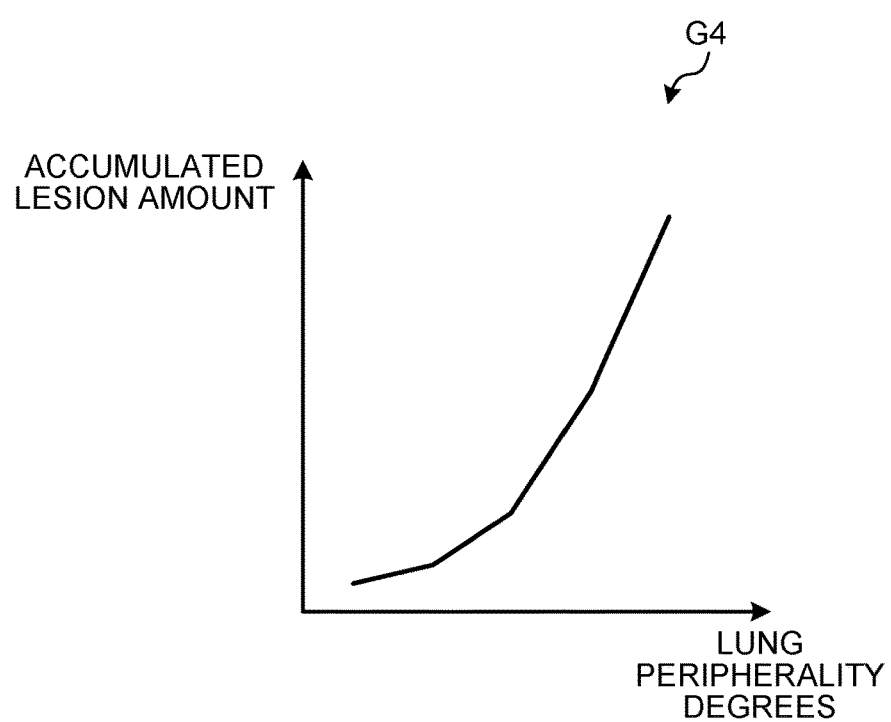
FIG. 10 is a graph illustrating yet another example of displaying a distribution of lesion amounts with respect to the anatomical structure according to the embodiment.

In a seventh embodiment, differences from the sixth embodiment will primarily be explained. FIG. 10 is a graph illustrating yet another example of the display of a distribution of lesion amounts with respect to the anatomical structure according to the embodiment. Similarly to FIG. 8, the graph in image G4 illustrated in FIG. 10 is a line graph. By using this display mode also, it is possible to achieve advantageous effects similar to those of the sixth embodiment.

Eighth Embodiment

When displaying the distribution information about the lesion amounts according to the embodiments described above, the display control function 447 may arbitrarily change the scale of the graph, on the basis of an input operation received from the operator via the input interface 43. In this situation, the scale of the graph denotes a region for which distribution information about lesion amounts is to be generated so as to be displayed in the graph. More specifically, the distribution information about the lesion amounts to be displayed in the graph may be generated and displayed with respect to regions corresponding to the entirety of the left and the right lungs, each of the left and the right lungs, each of the lung lobes, each of the lung segments, or the like. Further, the distribution information about the lesion amounts do not necessarily have to be generated and displayed with respect to the regions, buy may be generated and displayed as a graph in which information about a plurality of arbitrary regions can be referenced at a glance. By using this display mode also, it is possible to achieve advantageous effects similar to those of the embodiments described above.

Ninth Embodiment

In the above embodiments, the example was explained in which the distribution of the lesion amounts with respect to the peripherality degrees is displayed as the display of the distribution information about the lesion amounts; however, possible embodiments are not limited to this example. As the distribution information about the lesion amounts, it is also possible to display a distribution of peripherality degrees with respect to the lesion amounts. For example, the display control function 447 may interchange the axes of any of the graphs, on the basis of an input operation received from the operator via the input interface 43. By using this display mode also, it is possible to achieve advantageous effects similar to those of the embodiments described above. Further, in accordance with what the operator wishes to check, he/she is able to check the information by arbitrarily switching between the distribution of the lesion amounts along the extent of the bronchi and a certain peripherality degree exhibiting a large lesion amount, i.e., a certain position along the extent of the bronchi exhibiting a large lesion amount.

Tenth Embodiment

When displaying the distribution information about the lesion amounts according to the embodiments described above, the display control function 447 may cause the display 42 to further display a corresponding CT image. For example, the operator may designate an arbitrary point in the graph. In that situation, on the basis of the input operation received from the operator via the input interface 43, the display control function 447 causes the display 42 to display a CT image representing the designated point in the graph. The CT image representing the designated point in the graph may be, for example, a CT image having the peripherality degree at the designated point and indicating an MPR cross-section that passes through a representative point in the region where a lesion is present. More preferably, the CT image representing the designated point in the graph may be, for example, a CT image having the peripherality degree at the designated point and indicating an MPR cross-section that passes through a representative point in the region where the lesions are present in the largest amount. In this situation, the display control function 447 may display the CT image in place of the display of the graph or may display the CT image together with the graph. By using this display mode also, it is possible to achieve advantageous effects similar to those of the embodiments described above.

Eleventh Embodiment

When displaying the distribution information about the lesion amounts according to the embodiments described above, the display control function 447 may display, upon designation of a lung peripherality degree or a range of lung peripherality degrees in a graph, a lesion region having the peripherality degree or a lung peripherality degree in the range of peripherality degrees, so as to be highlighted in a CT image indicating an MPR cross-section or a three-dimensional CT image, for example. By using this display mode also, it is possible to achieve advantageous effects similar to those of the embodiments described above.

Twelfth Embodiment

When displaying the distribution information about the lesion amounts according to the embodiments described above, the display control function 447 may display, upon designation of a point within the CT image displayed as described above, a position in a graph corresponding to the designated point. In that situation, the peripherality calculation function 445 calculates a lung peripherality degree of the designated point. After that, the display control function 447 may display, in a highlighted manner, a position or a range in the graph corresponding to the calculated lung peripherality degree or may display an icon in the position or the range. By using this display mode also, it is possible to achieve advantageous effects similar to those of the embodiments described above.

Thirteenth Embodiment

Figure 11:
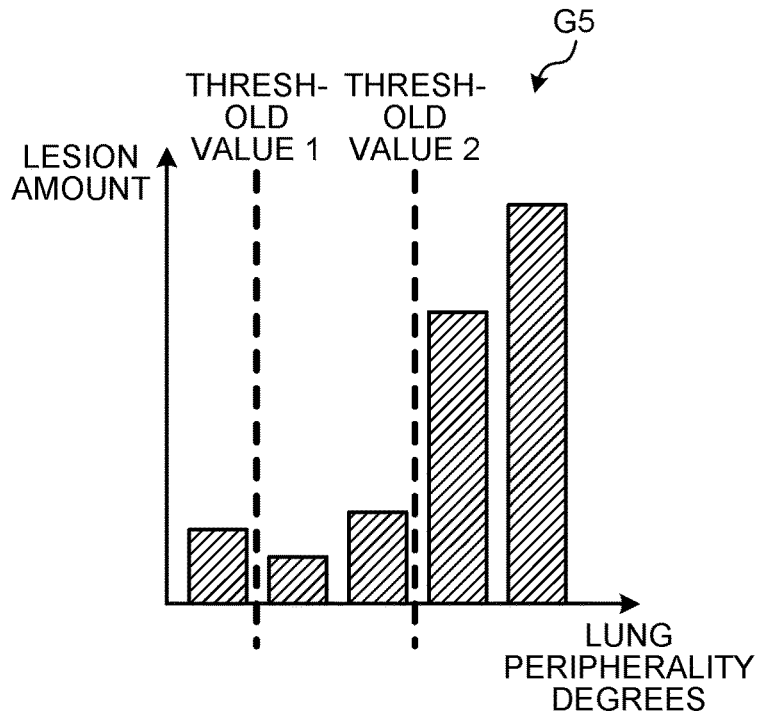
FIG. 11 is a graph illustrating an example of displaying a screen for designating a division number related to degrees of peripherality according to the embodiment.

The distribution information about the lesion amounts according to the embodiments described above may be calculated and displayed as being divided into arbitrary sections with respect to the peripherality degrees. FIG. 11 is a graph illustrating an example of displaying an operation screen for a division number related to the peripherality degrees. FIG. 11 illustrates an image G5 displayed when the operator has performed an input operation to change the display sections for the peripherality degrees in the image G1 of FIG. 4, from five divided sections to three divided sections. As illustrated in FIG. 11, in response to the input operation regarding threshold values received from the operator via the input interface 43, the display control function 447 causes the display 42 to further display the threshold values related to the display sections for the peripherality degrees. The input operation performed by the operator regarding the threshold values may be an operation to input the values of the peripherality degrees serving as the threshold values, may be an operation to input the division number, or may be an input operation on a GUI to change the positions of the icons indicating the threshold values within the image G5.

Figure 12:
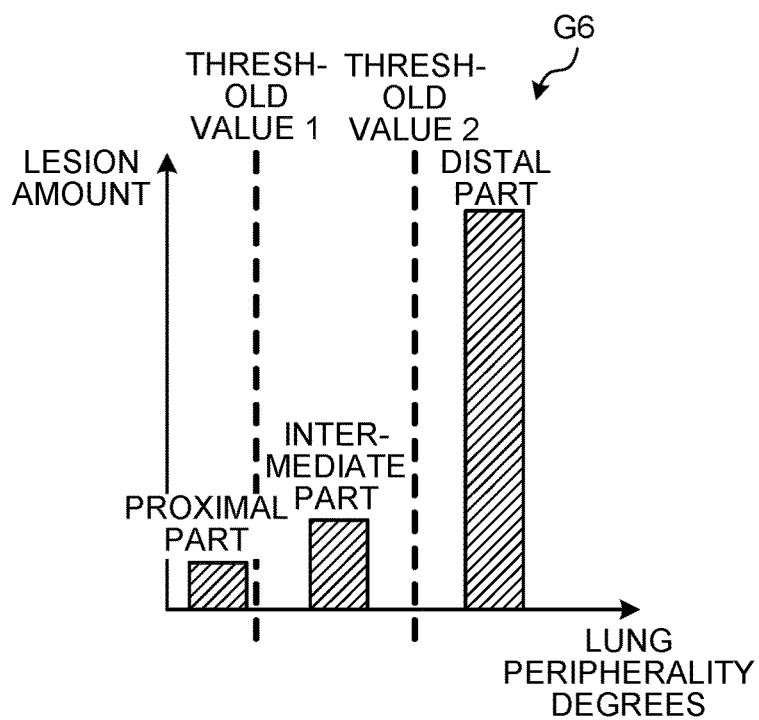
FIG. 12 is a graph illustrating yet another example of displaying a distribution of lesion amounts with respect to the anatomical structure according to the embodiment.

The lesion quantification function 446 re-generates distribution information about the lesion amounts on the basis of the threshold values for the peripherality degrees corresponding to the input operation. Further, the display control function 447 causes the display 42 to display the re-generated distribution information about the lesion amounts with respect to the anatomical structure. FIG. 12 is a graph illustrating yet another example of the display of the distribution of the lesion amounts with respect to the anatomical structure according to the embodiment. FIG. 12 illustrates an image G6 indicating the distribution information about the lesion amounts displayed with display sections divided into three, in accordance with the two threshold values being set.

As explained above, on the basis of the input operation received from the operator via the input interface 43, the display control function 447 is capable of arbitrarily changing the division number related to the peripherality degrees. According to the technique of the present embodiment, the display sections can be divided with the arbitrary peripherality degrees, no matter what the division number is. It is therefore possible to display the distribution information about the lesion amounts, so as to be divided into sections that are anatomically meaningful along the extent of the bronchi. By using this display mode also, it is possible to achieve advantageous effects similar to those of the embodiments described above.

In the example in FIG. 12, the peripherality degrees are divided into the three sections corresponding to a proximal part, an intermediate part, and a distal part; however, possible division numbers for the peripherality degrees are not limited to this example. The division number for the peripherality degrees may indicate division into two sections or multiple division into four or more sections. In this situation, the division number for the peripherality degrees may arbitrarily be set with respect to the regions for which the distribution information about the lesion amounts is to be generated and displayed, such as the entirety of the left and the right lungs, each of the left and the right lungs, each of the lung lobes, each of the lung segments, or the like.

Preferably, the peripherality degrees may be divided into two sections corresponding to a peripheral part and a central part for each of the lung lobes. In other words, the lesion amounts may be calculated with respect to each of a total of ten sections, i.e., two sections in each of the five lung lobes including the three lung lobes of the right lung and the two lung lobes of the left lung. In that situation, the distribution information about the lesion amounts may be generated and displayed as a graph of each of the lung lobes divided by one threshold value for each lung lobe or may be generated and displayed as a graph of the entirety of the left and the right lungs in which the lesion amounts of the ten sections can be referenced at a glance. As an alternative, preferably, the peripherality degrees may be divided into two sections corresponding to a peripheral part and a central part for each of the lung segments, instead of the lung lobes. In other words, the lesion amounts may be calculated with respect to each of a total of 36 sections, i.e., two sections in each of 18 lung segments. In that situation, the distribution information about the lesion amounts may be generated and displayed as a graph of each of the lung segments divided by one threshold value for each lung segment or may be generated and displayed as a graph of the entirety of the left and the right lungs in which the lesion amounts of the 36 sections can be referenced at a glance.

Fourteenth Embodiment

Figure 13:
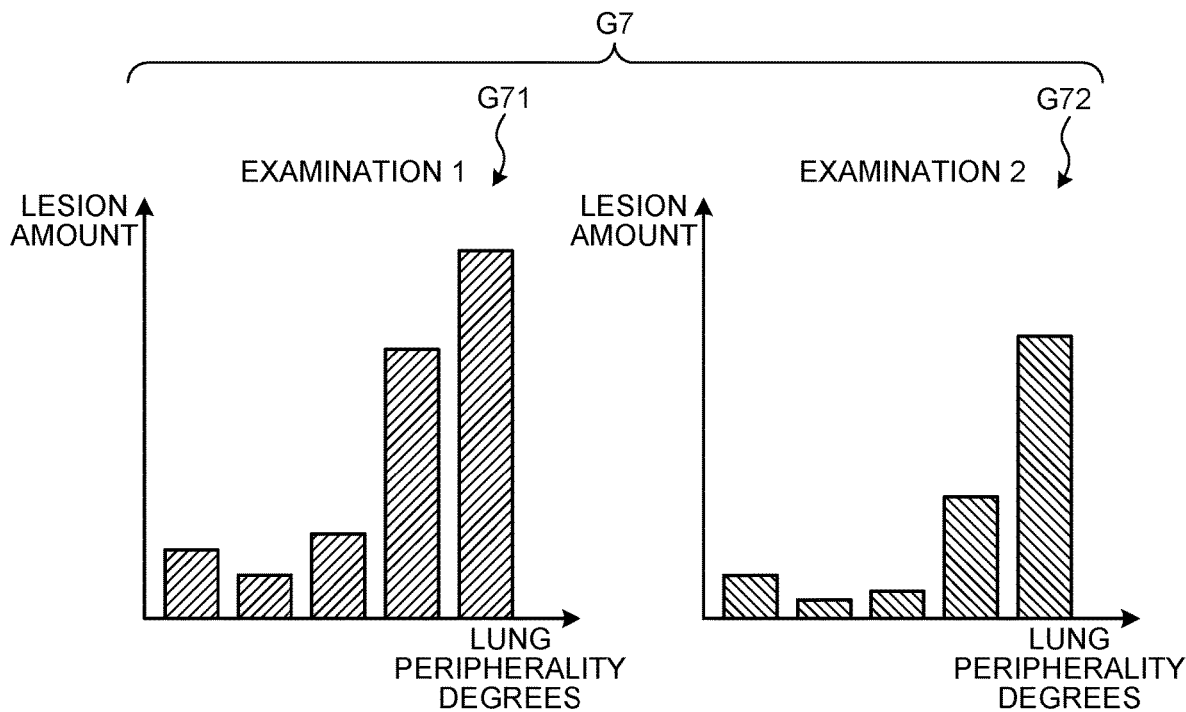
FIG. 13 is a graph illustrating yet another example of displaying a distribution of lesion amounts with respect to the anatomical structure according to the embodiment.

The X-ray CT apparatus 1 in which the medical information display apparatus or the medical image processing apparatus according to any of the embodiments described above is installed is also capable of calculating and displaying information indicating chronological changes in the distribution information about the lesion amounts with respect to the anatomical structure. FIG. 13 is a graph illustrating yet another example of the display of a distribution of the lesion amounts with respect to the anatomical structure according to the embodiment. As illustrated in FIG. 13, the display control function 447 may display an image G7 indicating chronological changes in the distribution of the lesion amounts with respect to the anatomical structure. The image G7 includes an image G71 displaying distribution information about lesion amounts related to "examination 1". Further, the image G7 includes an image G72 displaying distribution information about lesion amounts related to "examination 2" different from "examination 1". In this situation, the distribution information about the lesion amounts related to "examination 1" is distribution information about the lesion amounts generated on the basis of volume data acquired at a first point in time. Similarly, the distribution information about the lesion amounts related to "examination 2" is distribution information about the lesion amounts generated on the basis of volume data acquired at a second point in time different from the first point in time.

For example, the process of displaying the distribution information about the lesion amounts illustrated in FIG. 3 may be performed with respect to at least two pieces of volume data specified on the basis of an input operation received from the operator via the input interface 43. The processes related to the two pieces of volume data acquired at the mutually-different points in time may be performed in a single workflow or may be performed in separate workflows. In other words, the display control function 447 does not have to perform the processes at steps S101 through S105 in FIG. 3 again, with respect to the volume data from which distribution information about lesion amounts has already been generated. By using this display mode also, it is possible to achieve advantageous effects similar to those of the embodiments described above. Further, the operator is able to easily understand the chronological changes in the lesion amounts with respect to various peripherality degrees.

In this situation, the image G71 and the image G72 may be displayed simultaneously as in the image G7 illustrated in FIG. 13 or may be sequentially displayed on the basis of input operations received from the operator via the input interface 43.

Fifteenth Embodiment

Figure 14:
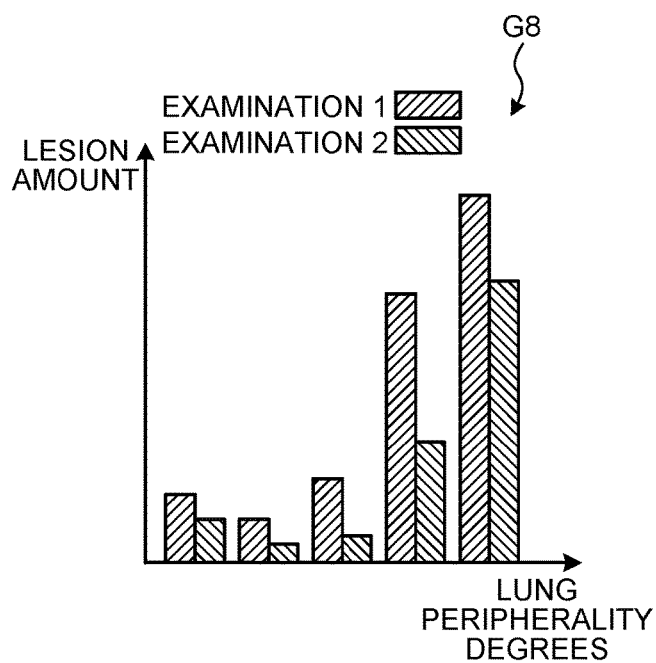
FIG. 14 is a graph illustrating yet another example of displaying a distribution of lesion amounts with respect to the anatomical structure according to the embodiment.

In a fifteenth embodiment, differences from the fourteenth embodiment will primarily be explained. FIG. 14 is a graph illustrating yet another example of the display of a distribution of lesion amounts with respect to the anatomical structure according to the embodiment. As illustrated in an image G8 in FIG. 14, the display control function 447 may display, in a single graph, the distribution information about the lesion amounts related to "examination 1" at the first point in time and the distribution information about the lesion amounts related to "examination 2" at the second point in time different from the first point in time. By using this display mode also, it is possible to achieve advantageous effects similar to those of the fourteenth embodiment.

Sixteenth Embodiment

Figure 15:
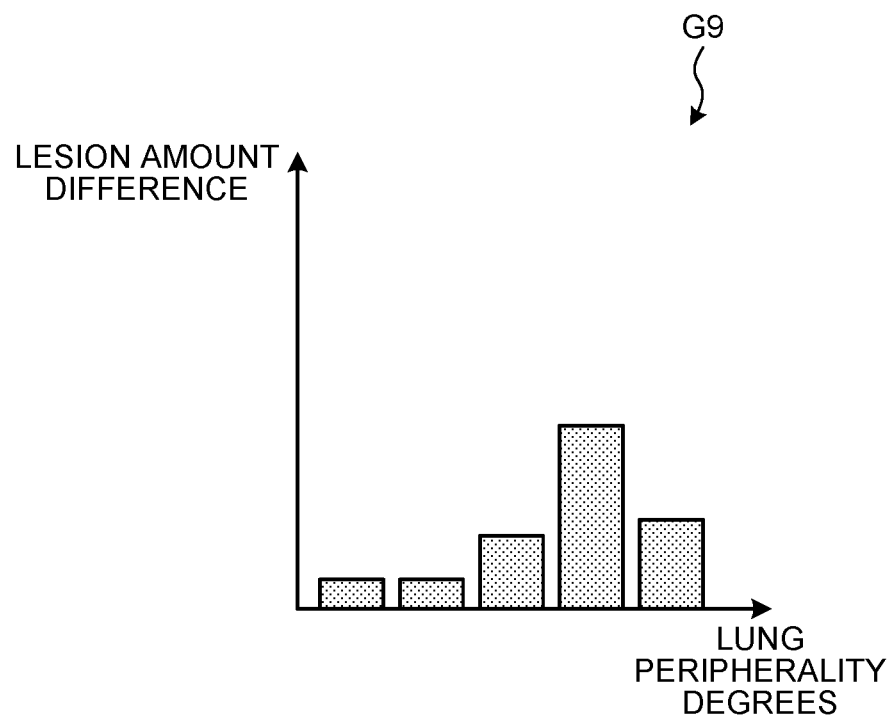
FIG. 15 is a graph illustrating yet another example of displaying a distribution of lesion amounts with respect to the anatomical structure according to the embodiment.

In a sixteenth embodiment, differences from the fourteenth embodiment will primarily be explained. FIG. 15 is a graph illustrating yet another example of the display of a distribution of lesion amounts with respect to the anatomical structure according to the embodiment. As illustrated in an image G9 in FIG. 15, the display control function 447 may display, in a single graph, differences in lesion amounts corresponding to various peripherality degrees between "examination 1" at the first point in time and "examination 2" at the second point in time different from the first point in time. In other words, the lesion quantification function 446 is configured to calculate a lung lesion amount corresponding to each of the various lung peripherality degrees from the pieces of volume data and to subsequently further calculate the differences in the lung lesion amounts corresponding to the various lung peripherality degrees. By using this display mode also, it is possible to achieve advantageous effects similar to those of the fourteenth embodiment.

With reference to FIGS. 13 to 15, the example was explained in which the information indicating the chronological changes in the distribution of the lesion amounts with respect to the anatomical structure is calculated and displayed on the basis of the two pieces of volume data acquired at the mutually-different points in time; however, possible embodiments are not limited to this example. The information indicating the chronological changes in the distribution of the lesion amounts with respect to the anatomical structure may be calculated and displayed on the basis of three or more pieces of volume data.

The processes of displaying the distribution information about the lesion amounts according to any of the embodiments described above may be used in combination. For example, the display control function 447 may arbitrarily switch between displays on the basis of an input operation received from the operator via the input interface 43. When an additional process occurs at the time of switching between the displays, the medical information display apparatus is configured to further acquire display-purpose information acquired in the processes described above. Further, the medical image processing apparatus is configured to further perform the processes related to the various types of displays described above and to further generate display-purpose information.

The term "processor" used in the above description means a circuit such as a CPU, a graphics processing unit (GPU), an ASIC, or a programmable logic device (PLD), for example. PLDs include simple programmable logic devices (SPLDs), complex programmable logic devices (CPLDs), and field programmable gate arrays (FPGAs). The processor implements its functions by reading and executing a computer program stored in a memory circuit. The storage circuit in which the computer program is stored is a computer-readable, non-transitory storage medium. In place of storing the computer program in the memory circuit, the computer program may directly be incorporated into the circuit of the processor. In this case, the processor implements its functions by reading and executing the computer program incorporated into the circuit. Not executing the computer program, the function corresponding to the computer program may be implemented by a combination of logic circuits. Each processor of the present embodiment is not limited to being configured as a single circuit for each processor and may be configured as one processor by combining a plurality of independent circuits to implement its functions. Furthermore, the components in FIG. 1 may be integrated into a single processor to implement their functions.

According to at least one aspect of the embodiments described above, it is possible to evaluate the distribution of the lesion amounts with respect to the anatomical structure.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the embodiments described above, the following notes are disclosed as an aspect and selected characteristics of the present disclosure.

Note 1:
A medical information display apparatus including first processing circuitry configured to display information on the basis of volume data including at least an organ, in which
 the first processing circuitry displays a first index value based on an anatomical structure of the organ and a second index value based on the volume data related to the organ, so as to be kept in correspondence with each other.

Note 2:
The anatomical structure of the organ may be a tubular tissue included in the organ.

Note 3:
The tubular tissue may have at least one branch.

Note 4:
The first index value may be an index value based on the quantity of branches of the tubular tissue.

Note 5:
The first index value may be an index value indicating a peripherality degree of the tubular tissue.

Note 6:
The first index value may be information defining a position within a tissue being included in the organ and being a surrounding tissue of the tubular tissue.

Note 7:
The position within the surrounding tissue of the tubular tissue may be information defining the position by using the extent of the tubular tissue as a reference.

Note 8:
The second index value may be an index value related to a lesion amount of the organ.

Note 9:
The second index value may be a voxel value or a pixel value satisfying a predetermined threshold value condition among voxel values of the volume data or pixel values of image data based on the volume data.

Note 10:
The voxel value or the pixel value may be a Computed Tomography (CT) value or a value based on the CT value.

Note 11:
Provided may be a medical image processing apparatus further including second processing circuitry configured to
 acquire the volume data;
 extract an anatomical structure of the organ included in the volume data;
 calculate the first index value at an arbitrary evaluation point in the volume data, on the basis of the extracted anatomical structure of the organ; and
 derive the second index value on the basis of the volume data.

Note 12:
The evaluation point may be set in the surrounding tissue.

Note 13:
The first index value may be calculated on the basis of a point that is in the tubular tissue and is positioned nearest to the evaluation point.

Note 14:
The first index value maybe the length measured of the tubular tissue from a reference point in the tubular tissue on the central side to a point in the tubular tissue on the peripheral side that is positioned nearest to the evaluation point.

Note 15:
The first index value may be the quantity of branches of the tubular tissue that are present between a reference point in the tubular tissue on the central side and a point in the tubular tissue on the peripheral side that is positioned nearest to the evaluation point.

Note 16:
The first index value may be the quantity of branches in a coupled region including the evaluation point, the coupled region being formed in the surrounding tissue by implementing a region growing method starting with a plurality of regions in the tubular tissue having an equal quantity of branches in the tubular tissue as counted from a reference point in the tubular tissue on the central side.

Note 17:
The reference point may be set at a branch positioned on the most central side in the tubular tissue.

Note 18:
The anatomical structure of the organ may be one selected from between: the outer shape of the organ; and the outer shape of an anatomical region of the organ.

Note 19:
The first index value may be one selected from between: the distance from an outer surface of the organ; and the distance from a boundary plane of an anatomical region of the organ.

Note 20:
The first index value may be one selected from between: a section of the distance from an outer surface of the organ; and a section of the distance from a boundary plane of an anatomical region of the organ.

Note 21:
When the organ is a lung, the anatomical structure of the organ may be the extent of a bronchus included in the lung.

Note 22:
The surrounding tissue of the tubular tissue may be the lung parenchyma included in the lung.

Note 23:
When the organ is one of the brain, the liver, and a kidney, the anatomical structure of the organ may be a blood vessel included in the organ.

Note 24:
A display may further be provided so as to display a first index value based on an anatomical structure of the organ and a second index value related to a lesion amount of the organ, so to be kept in correspondence with each other.

Note 25:
The display of the first index value and the second index value kept in correspondence with each other may include displaying a graph in which one of vertical and horizontal axes expresses the first index value, whereas the other of the two axes expresses the second index value.

Note 26:
The volume data may include two pieces of data acquired at mutually-different points in time.

Note 27:
The display of the first index value and the second index value kept in correspondence with each other may include display related to each of the two pieces of data.

Note 28:
The display of the first index value and the second index value kept in correspondence with each other may be display indicating a difference in the first index values or the second index values between the two pieces of data.

Note 29:
The kept in correspondence with each other may include graphically or pictorially representing how the second index varies with the first index.

Note 30:
A method for controlling the configurations of the abovementioned medical information display apparatus.

Note 31:
A method for controlling the configurations of the abovementioned medical image processing apparatus.

Note 32:
A program that causes a computer to execute the configurations of the abovementioned medical information display apparatus.

Note 33:
A program that causes a computer to execute the configurations of the abovementioned medical image processing apparatus.

Note 34:
A computer program product storing the abovementioned program executed by the computer.

What is claimed is:

1. A medical information display apparatus for displaying an index value for a lung, the medical information display apparatus comprising:
first processing circuitry configured to display information based on volume data including at least a lung, wherein
the first processing circuitry is further configured to display a first index value and a second index value, so as to be kept in correspondence with each other, the first index value being information defining a position within lung parenchyma included in the lung based on an extent of a bronchus included in the lung, the second index value being based on the volume data related to the lung.

2. The medical information display apparatus according to claim 1, wherein the second index value is an index value related to a lesion amount of the lung.

3. The medical information display apparatus according to claim 1, wherein the second index value is a Computed Tomography (CT) value satisfying a predetermined threshold value condition.

4. The medical information display apparatus according to claim 1, wherein the display, by the first processing circuitry, of the first index value and the second index value kept in correspondence with each other includes displaying a graph in which one of vertical and horizontal axes expresses the first index value, whereas the other of the two axes expresses the second index value.

5. The medical information display apparatus according to claim 1, wherein the volume data includes two pieces of data acquired at mutually-different points in time.

6. A medical image processing apparatus for deriving the index value for the lung, the medical image processing apparatus comprising:
the medical information display apparatus according to claim 1; and
second processing circuitry configured to:
acquire the volume data;
extract the extent of the bronchus included in the lung included in the volume data;
calculate the first index value at an arbitrary evaluation point in the volume data, based on the extracted extent of the bronchus included in the lung; and
derive the second index value based on the volume data.

7. The medical image processing apparatus according to claim 6, wherein
the second processing circuitry is further configured to calculate the first index value based on a length measured of the bronchus from a reference point in the bronchus on a central side to a point in the bronchus on a peripheral side that is positioned nearest to the evaluation point.

8. The medical image processing apparatus according to claim 6, wherein
the second processing circuitry is further configured to calculate, as the first index value, a quantity of branches of the bronchus that are present between a reference point in the bronchus on a central side and a point in the bronchus on a peripheral side that is positioned nearest to the evaluation point.

9. The medical image processing apparatus according to claim 8, wherein, when the evaluation point is included in a coupled region formed in the lung parenchyma included in the lung, by implementing a region growing method while using a plurality of regions in the bronchus having an equal quantity of branches as starting points, the second processing circuitry is further configured to calculate, as the first index value, the quantity of the branches in the regions in the bronchus serving as the starting points in the formation of the coupled region.

10. A medical information display method for displaying an index value for a lung based on volume data including at least the lung, the medical information display method comprising:
displaying a first index value and a second index value, so to be kept in correspondence with each other, the first index value being information defining a position within lung parenchyma included in the lung based on an extent of a bronchus included in the lung, the second index value being based on the volume data related to the lung.

11. The medical information display method according to claim 10, further comprising:
acquiring the volume data including at least the lung;
extracting the extent of the bronchus included in the lung included in the volume data;

calculating the first index value at an arbitrary evaluation point in the volume data, based on the extracted extent of the bronchus included in the lung; and deriving the second index value based on the volume data related to the lung.

* * * * *